United States Patent
Pigamo et al.

(10) Patent No.: US 10,207,969 B2
(45) Date of Patent: Feb. 19, 2019

(54) COMPOSITIONS CONTAINING 1,1,1,3,3-PENTACHLOROPROPANE

(71) Applicant: Arkema France, Colombes (FR)

(72) Inventors: Anne Pigamo, Francheville (FR); Dominique Deur-Bert, Charly (FR); Laurent Wendlinger, Soucieu en Jarrest (FR); Bertrand Collier, Saint-genis-laval (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/518,607

(22) PCT Filed: Oct. 7, 2015

(86) PCT No.: PCT/FR2015/052694
§ 371 (c)(1),
(2) Date: Apr. 12, 2017

(87) PCT Pub. No.: WO2016/059323
PCT Pub. Date: Apr. 21, 2016

(65) Prior Publication Data
US 2017/0226032 A1    Aug. 10, 2017

(30) Foreign Application Priority Data
Oct. 16, 2014 (FR) ..................... 14 59928

(51) Int. Cl.
*C07C 17/20* (2006.01)
*C07C 19/01* (2006.01)

(52) U.S. Cl.
CPC ............ *C07C 17/206* (2013.01); *C07C 19/01* (2013.01)

(58) Field of Classification Search
CPC .......... C07C 19/01; C07C 21/18; C07C 19/10
See application file for complete search history.

(56) References Cited

U.S. PATENT DOCUMENTS

| | | | |
|---|---|---|---|
| 5,705,779 A | 1/1998 | Demmin et al. | |
| 6,313,360 B1 * | 11/2001 | Wilson | C07C 17/278 570/257 |
| 2012/0059199 A1 | 3/2012 | Pokrovski et al. | |
| 2012/0172636 A1 * | 7/2012 | Pokrovski | C07C 17/206 570/135 |
| 2012/0184786 A1 | 7/2012 | Merkel et al. | |

FOREIGN PATENT DOCUMENTS

| EP | 2 341 040 | 7/2011 |
|---|---|---|
| WO | WO-2012/098421 | 7/2012 |
| WO | WO-2014/094590 | 6/2014 |

OTHER PUBLICATIONS

International Search Report dated Jan. 21, 2016 for PCT/FR2015/052694.

* cited by examiner

*Primary Examiner* — Jafar F Parsa
(74) *Attorney, Agent, or Firm* — NK Patent Law

(57) ABSTRACT

The invention first relates to a composition comprising at least 99 wt. % of 1,1,1,3,3-pentachloropropane and at least one compound selected from a list of additional compounds consisting of dichloropropanes, trichloropropanes, tetrachloropropanes, pentachloropropanes different from 1,1,1,3,3-pentachloropropane, hexachloropropanes, heptachloropropanes, chloropropenes, dichloropropenes, trichloropropenes, tetrachloropropenes, pentachloropropenes and hexachloropropene, the weight content of said compound in the composition being lower than or equal to 500 ppm.

11 Claims, No Drawings

COMPOSITIONS CONTAINING 1,1,1,3,3-PENTACHLOROPROPANE

CROSS-REFERENCE TO RELATED APPLICATIONS

This application is a U.S. National Stage application of International Application No. PCT/FR2015/052694, filed Oct. 7, 2015, which claims the benefit of French Application No. 1459928, filed Oct. 16, 2014.

FIELD OF THE INVENTION

The present invention relates to compositions based on F-240fa (1,1,1,3,3 -pentachloropropane) and also to the use thereof especially for producing F-1233zdE (trans-1-chloro-3,3,3-trifluoropropene) and/or F-1234zeE (trans-1,3,3,3-tetrafluoropropene).

TECHNICAL BACKGROUND

Fluoroolefins F-1233zdE and F-1234zeE are compounds of major interest for refrigeration and air conditioning systems, given the new environmental regulations.

It is known practice to produce hydrofluoroolefins such as F-1233zdE and/or by fluorination of hydrochloroolefins or chlorohydrocarbons, especially. This fluorination is generally a catalytic fluorination using hydrofluoric acid as fluorinating agent.

Among the routes for obtaining F-1233zdE, it is in particular known practice to use F-240fa (1,1,1,3,3-pentachloropropane) as starting compound. Reference is made, for example, to U.S. Pat. No. 8,704,017 in this respect, which describes a process for fluorination in the liquid phase in the absence of catalyst.

Another possible process is gas-phase fluorination in the presence of a catalyst and of an oxidizing agent, such as chlorine, for example, in order to maintain the stability of the catalyst.

Furthermore, it is known to use the compound F-1233zdE for the successive production of F-1234zeE. Reference is made, for example, to U.S. Pat. No. 5,895,825 in this respect.

It is desirable to be able to produce F-1233zdE with a low content of impurities. In particular, the formation of certain toxic and/or flammable impurities and/or impurities liable to polymerize and/or impurities that are difficult to separate from F-1233zdE should be minimized.

It is also desirable to be able to produce F-1234zeE with a low content of impurities. In particular, the formation of certain toxic impurities and/or impurities liable to polymerize and/or impurities that are difficult to separate from F-1234zeE should be minimized.

There is thus a need to provide means for obtaining F-1233zdE and F-1234zeE compositions of satisfactory purity.

SUMMARY OF THE INVENTION

The invention relates firstly to a composition comprising at least 99% by weight of 1,1,1,3,3-pentachloropropane, and comprising at least one compound chosen from a list of additional compounds consisting of dichloropropanes, trichloropropanes, tetrachloropropanes, pentachloropropanes other than 1,1,1,3,3-pentachloropropane, hexachloropropanes, heptachloropropanes, chloropropenes, dichloropropenes, trichloropropenes, tetrachloropropenes, pentachloropropenes and hexachloropropene, said compound being present in the composition in a weight content of less than or equal to 500 ppm.

According to one embodiment, said compound is present in the composition in a weight content of less than or equal to 250 ppm; preferably less than or equal to 150 ppm; more particularly less than or equal to 100 ppm; more particularly less than or equal to 50 ppm; and ideally less than or equal to 10 ppm.

According to one embodiment, the composition comprises a plurality of compounds chosen from said list of additional compounds, each of the compounds of said plurality of compounds being present in the composition in a weight content of less than or equal to 500 ppm; preferably less than or equal to 250 ppm; preferably less than or equal to 150 ppm; more particularly less than or equal to 100 ppm; more particularly less than or equal to 50 ppm; and ideally less than or equal to 10 ppm.

According to one embodiment, the composition comprises a plurality of compounds chosen from said list of additional compounds, the total weight content of all of the compounds of said list being less than or equal to 1000 ppm; preferably less than or equal to 500 ppm; preferably less than or equal to 250 ppm; preferably less than or equal to 150 ppm; more particularly less than or equal to 100 ppm; more particularly less than or equal to 50 ppm; and ideally less than or equal to 10 ppm.

According to one embodiment, the composition comprises at least 99.5% by weight, preferably at least 99.8% by weight, and more particularly preferably at least 99.9% by weight, of 1,1,1,3,3-pentachloropropane.

According to one embodiment, the composition comprises at least one compound chosen from the group consisting of hexachloropropene and heptachloropropanes, and the weight content of each of these compounds in the composition is less than or equal to 500 ppm, preferably less than or equal to 200 ppm, more particularly less than or equal to 100 ppm and ideally less than or equal to 50 ppm; and optionally, the total weight content of the compounds of this group in the composition is less than or equal to 500 ppm, preferably less than or equal to 200 ppm, more particularly less than or equal to 100 ppm and ideally less than or equal to 50 ppm.

According to one embodiment, the composition comprises at least one compound chosen from the group consisting of pentachloropropenes and hexachloropropanes, and the weight content of each of these compounds in the composition is less than or equal to 500 ppm, preferably less than or equal to 200 ppm, more particularly less than or equal to 100ppm and ideally less than or equal to 50 ppm; and, optionally, the total weight content of the compounds of this group in the composition is less than or equal to 500 ppm, preferably less than or equal to 200 ppm, more particularly less than or equal to 100ppm and ideally less than or equal to 50 ppm.

According to one embodiment, the composition comprises at least one compound chosen from the group consisting of tetrachloropropenes and pentachloropropanes other than 1,1,1,3,3-pentachloropropane, and the weight content of each of these compounds in the composition is less than or equal to 500 ppm, preferably less than or equal to 200 ppm, more particularly less than or equal to 100 ppm and ideally less than or equal to 50 ppm; and, optionally, the total weight content of the compounds of this group in the composition is less than or equal to 500 ppm, preferably less than or equal to 200 ppm, more particularly less than or equal to 100 ppm and ideally less than or equal to 50 ppm.

According to one embodiment, the composition comprises at least one compound chosen from the group consisting of 2,3,3,3-tetrachloropropene, 1,1,2,3-tetrachloropropene, 1,1,1,2,3-pentachloropropane, 1,1,2,2,3-pentachloropropane and 1,1,1,2,2-pentachloropropane, and the weight content of each of these compounds in the composition is less than or equal to 500 ppm, preferably less than or equal to 200 ppm, more particularly less than or equal to 100 ppm and ideally less than or equal to 50 ppm; and, optionally, the total weight content of the compounds of this group in the composition is less than or equal to 500 ppm, preferably less than or equal to 200 ppm, more particularly less than or equal to 100 ppm and ideally less than or equal to 50 ppm.

According to one embodiment, the composition comprising at least one compound chosen from the group consisting of trichloropropenes and tetrachloropropanes, and the weight content of each of these compounds in the composition is less than or equal to 500 ppm, preferably less than or equal to 200 ppm, more particularly less than or equal to 100 ppm and ideally less than or equal to 50 ppm; and, optionally, the total weight content of the compounds of this group in the composition is less than or equal to 500 ppm, preferably less than or equal to 200 ppm, more particularly less than or equal to 100 ppm and ideally less than or equal to 50 ppm.

According to one embodiment, the composition comprises at least one compound chosen from the group consisting of 1,1,3-trichloropropene, 3,3,3-trichloropropene, 1,1,1,3-tetrachloropropane, 1,1,2,3-tetrachloropropane and 1,1,1,2-tetrachloropropane, and the weight content of each of these compounds in the composition is less than or equal to 500 ppm, preferably less than or equal to 200 ppm, more particularly less than or equal to 100 ppm and ideally less than or equal to 50 ppm; and, optionally, the total weight content of the compounds of this group in the composition is less than or equal to 500 ppm, preferably less than or equal to 200 ppm, more particularly less than or equal to 100 ppm and ideally less than or equal to 50 ppm.

The invention also relates to a process for producing 1,3,3,3-tetrafluoropropene, especially in trans form, comprising:
  the provision of a composition as defined above;
  the reaction of this composition with hydrofluoric acid, preferably in the gas phase.

According to one embodiment, the process comprises a single step of catalytic fluorination.

According to one embodiment, the process comprises two successive steps of catalytic fluorination, namely:
  the reaction of the composition with hydrofluoric acid in the gas phase, to manufacture an intermediate product;
  optionally, purification of the intermediate product; and then
  reaction of the intermediate product with hydrofluoric acid in the gas phase, to manufacture 1,3,3,3-tetrafluoropropene;
  the intermediate product preferably being 1-chloro-3,3,3-trifluoropropene, especially in trans form.

The present invention makes it possible to overcome the drawbacks of the prior art. It more particularly provides compositions based on F-240fa, the content of impurities of which makes it possible to minimize the presence of harmful impurities in F-1233zdE or in F-1234zeE manufactured therefrom.

Specifically, the impurities present in F-1233zdE or in F-1234zeE are partly dependent on the impurities initially present in the F-240fa which is used to manufacture them.

In the course of the fluorination reaction(s), some of the impurities of F-240fa may be converted into different impurities in F-1233zdE or in F-1234zeE. Controlling the impurities present in F-240fa thus makes it possible indirectly to control the impurities present in F-1233zdE and in F-1234zeE.

Such an indirect control may be advantageous insofar as the impurities of F-1233zdE may be more difficult to separate from F-1233zdE than the impurities of F-240fa relative to F-240fa; and insofar as the impurities of F-1234zeE may be more difficult to separate from F-1234zeE than the impurities of F-240fa relative to F-240fa. This is especially the case when the impurities of F-1233zdE (respectively the impurities of F-1234zeE) have a very close boiling point or form an azeotrope or a quasi-azeotrope with F-1233zdE (respectively F-1234zeE).

DESCRIPTION OF EMBODIMENTS OF THE INVENTION

The invention is now described in greater detail and in a nonlimiting manner in the description that follows.

All the contents indicated are weight contents, unless otherwise mentioned.

Nomenclature

The table below gives the nomenclature of a certain number of compounds that are included in the invention.

| Formula | Notation | Full name |
|---|---|---|
| $CCl_3$—$CHCl$—$CCl_3$ | F-220da | 1,1,1,2,3,3,3-heptachloropropane |
| $CHCl_2$—$CCl_2$—$CCl_3$ | F-220aa | 1,1,1,2,2,3,3-heptachloropropane |
| $CF_3$—$CHCl$—$CF_3$ | F-226da | 2-chloro-1,1,1,3,3,3-hexafluoropropane |
| $CF_3$—$CHF$—$CClF_2$ | F-226ea | 1-chloro-1,1,2,3,3,3-hexafluoropropane |
| $CF_3$—$CFCl$—$CHF_2$ | F-226ba | 2-chloro-1,1,2,3,3,3-hexafluoropropane |
| $CF_3$—$CF_2$—$CHFCl$ | F-226ca | 3-chloro-1,1,1,2,2,3-hexafluoropropane |
| $CClF_2$—$CF_2$—$CHF_2$ | F-226cb | 1-chloro-1,1,2,2,3,3-hexafluoropropane |
| $CCl_3$—$CH_2$—$CCl_3$ | F-230fa | 1,1,1,3,3,3-hexachloropropane |
| $CHCl_2$—$CHCl$—$CCl_3$ | F-230da | 1,1,1,2,3,3-hexachloropropane |
| $CHCl_2$—$CCl_2$—$CHCl_2$ | F-230aa | 1,1,2,2,3,3-hexachloropropane |
| $CH_2Cl$—$CCl_2$—$CCl_3$ | F-230ab | 1,1,1,2,2,3-hexachloropropane |
| $CF_3$—$CH_2$—$CF_3Cl$ | F-235fa | 3-chloro-1,1,1,3,3-pentafluoropropane |
| $CF_3$—$CHF$—$CHFCl$ | F-235ea | 1-chloro-1,2,3,3,3-pentafluoropropane |
| $CHF_2$—$CHF$—$CClF_2$ | F-235eb | 1-chloro-1,1,2,3,3-pentafluoropropane |
| $CHClF$—$CF_2$—$CHF_2$ | F-235ca | 3-chloro-1,1,2,2,3-pentafluoropropane |
| $CH_2Cl$—$CF_2$—$CF_3$ | F-235cb | 3-chloro-1,1,1,2,2-pentafluoropropane |
| $CH_2F$—$CF_2$—$CClF_2$ | F-235cc | 1-chloro-1,1,2,2,3-pentafluoropropane |
| $CHF2$—$CHCl$—$CF_3$ | F-235da | 2-chloro-1,1,1,3,3-pentafluoropropane |
| $CHF2$—$CClF$—$CHF_2$ | F-235ba | 2-chloro-1,1,2,3,3-pentafluoropropane |
| $CH_2F$—$CClF$—$CF_3$ | F-235bb | 2-chloro-1,1,1,2,3-pentafluoropropane |
| $CF_3$—$CH_2$—$CF_3$ | F-236fa | 1,1,1,3,3,3-hexafluoropropane |
| $CHF_2$—$CF_2$—$CHF_2$ | F-236ca | 1,1,2,2,3,3-hexafluoropropane |
| $CH_2F$—$CF_2$—$CF_3$ | F-236cb | 1,1,1,2,2,3-hexafluoropropane |
| $CHF_2$—$CHF$—$CF_3$ | F-236ea | 1,1,1,2,3,3-hexafluoropropane |
| $CHCl_2$—$CH_2$—$CCl_3$ | F-240fa | 1,1,1,3,3-pentachloropropane |
| $CHCl_2$—$CHCl$—$CHCl_2$ | F-240da | 1,1,2,3,3-pentachloropropane |
| $CH_2Cl$—$CHCl$—$CCl_3$ | F-240db | 1,1,1,2,3-pentachloropropane |
| $CH_2Cl$—$CCl_2$—$CHCl_2$ | F-240aa | 1,1,2,2,3-pentachloropropane |
| $CH_3$—$CCl_2$—$CCl_3$ | F-240ab | 1,1,1,2,2-pentachloropropane |
| $CH_2F$—$CF_2$—$CHF_2$ | F-245ca | 1,1,2,2,3-pentafluoropropane |

-continued

| Formula | Notation | Full name |
|---|---|---|
| CF₃—CF₂—CH₃ | F-245cb | 1,1,1,2,2-pentafluoropropane |
| CHF₂—CHF—CHF₂ | F-245ea | 1,1,2,3,3-pentafluoropropane |
| CH₂F—CHF—CF₃ | F-245eb | 1,1,1,2,3-pentafluoropropane |
| CHF₂—CH₂—CF₃ | F-245fa | 1,1,1,3,3-pentafluoropropane |
| CHCl₂—CH₂—CHCl₂ | F-250fa | 1,1,3,3-tetrachloropropane |
| CH₂Cl—CH₂—CCl₃ | F-250fb | 1,1,1,3-tetrachloropropane |
| CH₂Cl—CHCl—CHCl₂ | F-250da | 1,1,2,3-tetrachloropropane |
| CH₃—CHCl—CCl₃ | F-250db | 1,1,1,2-tetrachloropropane |
| CH₂Cl—CCl₂—CH₂Cl | F-250aa | 1,2,2,3-tetrachloropropane |
| CH₃—CCl₂—CHCl₂ | F-250ab | 1,1,2,2-tetrachloropropane |
| CF₂Cl—CH₂—CH₂F | F-253fa | 1-chloro-1,1,3-trifluoropropane |
| CH₂Cl—CH₂—CF₃ | F-253fb | 1-chloro-3,3,3-trifluoropropane |
| CF₂Cl—CH₂—CH₂F | F-253fc | 1-chloro-1,1,3-trifluoropropane |
| CH₂F—CClF—CH₂F | F-253ba | 2-chloro-1,2,3-trifluoropropane |
| CHF₂—CClF—CH₃ | F-253bb | 2-chloro-1,1,2-trifluoropropane |
| CH₂Cl—CF₂—CH₂F | F-253ca | 1-chloro-2,2,3-trifluoropropane |
| CHFCl—CF₂—CH₃ | F-253cb | 1-chloro-1,2,2-trifluoropropane |
| CHF₂—CHF—CH₂Cl | F-253ea | 3-chloro-1,1,2-trifluoropropane |
| CHClF—CHF—CH₂F | F-253eb | 1-chloro-1,2,3-trifluoropropane |
| CClF₂—CHF—CH₃ | F-253ec | 1-chloro-1,1,2-trifluoropropane |
| CH₂Cl—CH₂—CHCl₂ | F-260fa | 1,1,3-trichloropropane |
| CH₃—CH₂—CCl₃ | F-260fb | 1,1,1-trichloropropane |
| CH₂Cl—CHCl—CH₂Cl | F-260da | 1,2,3-trichloropropane |
| CH₃—CHCl—CHCl₂ | F-260db | 1,1,2-trichloropropane |
| CH₃—CCl₂—CH₂Cl | F-260aa | 1,2,2-trichloropropane |
| CH₂Cl—CH₂—CH₂Cl | F-270fa | 1,3-dichloropropane |
| CH₃—CH₂CHCl₂ | F-270fb | 1,1-dichloropropane |
| CH₃—CHCl—CH₂Cl | F-270da | 1,2-dichloropropane |
| CH₃—CCl₂—CH₃ | F-270aa | 2,2-dichloropropane |
| CCl₃—CCl=CCl₂ | F-1210xa | hexachloropropene |
| CF₃—CCl=CCl₂ | F-1213xa | 1,1,2-trichloro-3,3,3-trifluoropropene |
| CF₂Cl—CCl=CFCl | F-1213xb | 1,2,3-trichloro-1,3,3-trifluoropropene |
| CFCl₂—CCl=CF₂ | F-1213xc | 2,3,3-trichloro-1,1,3-trifluoropropene |
| CCl₃—CF=CF₂ | F-1213yc | 3,3,3-trichloro-1,1,2-trifluoropropene |
| CFCl₂—CF=CFCl | F-1213yb | 1,3,3-trichloro-1,2,3-trifluoropropene |
| CF₂Cl—CF=CCl₂ | F-1213ya | 1,1,3-trichloro-2,3,3-trifluoropropene |
| CCl₂F—CF=CF₂ | F-1214yc | 3,3-dichloro-1,1,2,3-tetrafluoropropene |
| CClF₂—CCl=CF₂ | F-1214xc | 2,3-dichloro-1,1,3,3-tetrafluoropropene |
| CClF₂—CF=CFCl | F-1214yb | 1,3-dichloro-1,2,3,3-tetrafluoropropene |
| CF₃—CCl=CFCl | F-1214xb | 1,2-dichloro-1,3,3,3-tetrafluoropropene |
| CF₃—CF=CCl₂ | F-1214ya | 1,2-dichloro-2,3,3,3-tetrafluoropropene |
| CF₃—CCl=CF₂ | F-1215xc | 2-chloro-1,1,3,3,3,-pentafluoropropene |
| CF₂—Cl—CF=CF₂ | F-1215yc | 3-chloro-1,1,2,3,3,-pentafluoropropene |
| CF₃—CF=CFCl | F-1215yb | 1-chloro-1,2,3,3,3,-pentafluoropropene |
| CF₃—CF=CF₂ | F-1216yc | hexafluoropropene |
| CHCl₂—CCl=CCl₂ | F-1220xa | 1,1,2,3,3-pentachloropropene |
| CCl₃—CCl=CHCl | F-1220xd | 1,2,3,3,3-pentachloropropene |
| CCl₃—CH=CCl₂ | F-1220za | 1,1,3,3,3-pentachloropropene |
| CF₃—CCl=CHCl | F-1223xd | 1,2-dichloro-3,3,3-trifluoropropene |
| CF₂Cl—CCl=CHF | F-1223xe | 2,3-dichloro-1,3,3-trifluoropropene |
| CHFCl—CCl=CF₂ | F-1223xc | 2,3-dichloro-1,1,3-trifluoropropene |
| CFCl₂—CH=CF₂ | F-1223zc | 3,3-dichloro-1,1,3-trifluoropropene |
| CF₂Cl—CH=CFCl | F-1223zb | 1,3-dichloro-1,3,3-trifluoropropene |
| CF₃—CH=CCl₂ | F-1223za | 1,1-dichloro-3,3,3-trifluoropropene |
| CHF₂—CF=CCl₂ | F-1223ya | 1,1-dichloro-2,3,3-trifluoropropene |
| CF₂Cl—CF=CHCl | F-1223yd | 1,3-dichloro-2,3,3-trifluoropropene |
| CFCl₂—CF=CHF | F-1223ye | 3,3-dichloro-1,2,3-trifluoropropene |
| CHCl₂—CF=CF₂ | F-1223yc | 3,3-dichloro-1,1,2-trifluoropropene |
| CHFCl—CF=CF₂ | F-1224yc | 3-chloro-1,1,2,3-tetrafluoropropene |
| CHF₂—CCl=CF₂ | F-1224xc | 2-chloro-1,1,3,3-tetrafluoropropene |
| CF₂Cl—CH=CF₂ | F-1224zc | 3-chloro-1,1,3,3-tetrafluoropropene |
| CHF₂—CF=CFCl | F-1224yb | 1-chloro-1,2,3,3-tetrafluoropropene |
| CF₃—CH=CFCl | F-1224zb | 1-chloro-1,3,3,3-tetrafluoropropene |
| CClF₂—CF=CHF | F-1224ye | 3-chloro-1,2,3,3-tetrafluoropropene |
| CF₃—CCl=CHF | F-1224xe | 2-chloro-1,3,3,3-tetrafluoropropene |
| CF₃—CF=CHCl | F-1224yd | 1-chloro-2,3,3,3-tetrafluoropropene |
| CF₃—CH=CF₂ | F-1225zc | 1,1,3,3,3-pentafluoropropene |
| CHF₂—CF=CF₂ | F-1225yc | 1,1,2,3,3-pentafluoropropene |
| CF₃—CF=CHF | F-1225ye | 1,2,3,3,3-pentafluoropropene |
| CH₂Cl—CCl=CCl₂ | F-1230xa | 1,1,2,3-tetrachloropropene |
| CHCl₂—CCl=CHCl | F-1230xd | 1,2,3,3-tetrachloropropene |
| CCl₃—CH=CH₂ | F-1230xf | 1,3,3,3-tetrachloropropene |
| CHCl₂—CH=CCl₂ | F-1230za | 1,1,3,3-tetrachloropropene |
| CCl₃—CH=CHCl | F-1230zd | 1,3,3,3-tetrachloropropene |
| CF₃—CCl=CH₂ | F-1233xf | 2-chloro-3,3,3-trifluoropropene |
| CClF₂—CF=CH₂ | F-1233yf | 3-chloro-2,3,3-trifluoropropene |
| CHF₂—CF=CHCl | F-1233yd | 1-chloro-2,3,3-trifluoropropene |
| CF₃—CH=CHCl | F-1233zd | 1-chloro-3,3,3-trifluoropropene |
| CHF₂—CCl=CHF | F-1233xe | 2-chloro-1,3,3-trifluoropropene |
| CHClF—CF=CHF | F-1233ye | 3-chloro-1,2,3-trifluoropropene |
| CClF₂—CH=CHF | F-1233ze | 3-chloro-1,1,3-trifluoropropene |
| CH₂Cl—CF=CF₂ | F-1233yc | 3-chloro-1,1,2-trifluoropropene |
| CFH₂—CCl=CF₂ | F-1233xc | 2-chloro-1,1,3-trifluoropropene |
| CFClH—CH=CF₂ | F-1233zc | 3-chloro-1,1,3-trifluoropropene |
| CFH₂—CF=CFCl | F-1233yb | 1-chloro-1,2,3-trifluoropropene |
| CF₂H—CH=CFCl | F-1233zb | 1-chloro-1,3,3-trifluoropropene |
| CF₃—CF=CH₂ | F-1234yf | 2,3,3,3-tetrafluoropropene |
| CF₃—CH=CHF | F-1234ze | 1,3,3,3-tetrafluoropropene |
| CH₂F—CF=CF₂ | F-1234yc | 1,1,2,3-tetrafluoropropene |
| CHF₂—CH=CF₂ | F-1234zc | 1,1,3,3-tetrafluoropropene |
| CHF₂—CF=CHF | F-1234ye | 1,2,3,3-tetrafluoropropene |
| CH₃—CCl=CCl₂ | F-1240xa | 1,1,2-trichloropropene |
| CH₂Cl—CCl=CHCl | F-1240xd | 1,2,3-trichloropropene |
| CHCl₂—CCl=CH₂ | F-1240xf | 2,3,3-trichloropropene |
| CH₂Cl—CH=CCl₂ | F-1240za | 1,1,3-trichloropropene |
| CHCl₂—CH=CHCl | F-1240zd | 1,3,3-trichloropropene |
| CCl₃—CH=CH₂ | F-1240zf | 3,3,3-trichloropropene |
| CClF₂—CH=CH₂ | F-1242zf | 3-chloro-3,3-difluoropropene |
| CHClF—CF=CH₂ | F-1242yf | 3-chloro-2,3-difluoropropene |
| CHF₂—CCl=CH₂ | F-1242xf | 2-chloro-3,3-difluoropropene |
| CH₃—CCl=CF₂ | F-1242xc | 2-chloro-1,1-difluoropropene |
| CH₂Cl—CH=CF₂ | F-1242zc | 3-chloro-1,1-difluoropropene |
| CH₂Cl—CF=CHF | F-1242ye | 3-chloro-1,2-difluoropropene |
| CH₂F—CCl=CHF | F-1242xe | 2-chloro-1,3-difluoropropene |
| CHFCl—CH=CHF | F-1242ze | 3-chloro-1,3-difluoropropene |
| CH₂F—CF=CHCl | F-1242yd | 1-chloro-2,3-difluoropropene |
| CHF₂—CH=CHCl | F-1242zd | 1-chloro-3,3-difluoropropene |
| CH₂F—CH=CF₂ | F-1243zc | 1,1,3-trifluoropropene |
| CH₃—CF=CF₂ | F-1243yc | 1,1,2-trifluoropropene |
| CF₃—CH=CH₂ | F-1243zf | 3,3,3-trifluoropropene |
| CH₂F—CF=CHF | F-1243ye | 1,2,3-trifluoropropene |
| CHF₂—CF=CH₂ | F-1243yf | 2,3,3-trifluoropropene |
| CHF₂—CH=CHF | F-1243ze | 1,3,3-trifluoropropene |
| CH₃—CH=CCl₂ | F-1250za | 1,1-dichloropropene |
| CH₃—CCl=CHCl | F-1250xd | 1,2-dichloropropene |
| CH₂Cl—CCl=CH₂ | F-1250xf | 2,3-dichloropropene |
| CH₂Cl—CH=CHCl | F-1250zd | 1,3-dichloropropene |
| CHCl₂—CH=CH₂ | F-1250zf | 3,3-dichloropropene |
| CH₃—CH=CF₂ | F-1252zc | 1,1-difluoropropene |
| CH₃—CF=CHF | F-1252ye | 1,2-difluoropropene |
| CH₂F—CF=CH₂ | F-1252yf | 2,3-difluoropropene |

-continued

| Formula | Notation | Full name |
|---|---|---|
| $CHF_2-CH=CH_2$ | F-1252zf | 3,3-difluoropropene |
| $CH_3-CCl=CH_2$ | F-1260xf | 2-cloropropene |
| $CH_3-CH=CHCl$ | F-1260zd | 1-cloropropene |
| $CH_2Cl-CH=CH_2$ | F-1260zf | 3-cloropropene |

When the above compounds exist in the form of two cis and trans isomers, the name of the compound (for example F-1234ze) denotes, without preference, one or the other form or a mixture of the two forms, and the maximum contents indicated are then total contents with respect to the two possible forms—except when the form is clarified by the letter E or Z.

Moreover, the name "F-220" generically denotes all of the heptachloropropane compounds, the name "F-230" generically denotes all of the hexachloropropane compounds, and so on, using the notations of the above table without the final two letters.

Compositions According to the Invention

The invention proposes compositions based on F-240fa. The content of F-240fa is greater than or equal to 99%.

According to certain embodiments, it is greater than or equal to 99.1%, or to 99.2%, or to 99.3%, or to 99.4%, or to 99.5%, or to 99.6%, or to 99.7%, or to 99.8%, or to 99.9%, or to 99.95%.

The compositions according to the invention also comprise at least one compound chosen from a list of additional compounds which is constituted by the series F-220, F-230, F-240 (with the exception of F-240fa), F-250, F-260, F-270 and by the series F-1210, F-1220, F-1230 (with the exception of F-1230za and F-1230zd, which may optionally be present in larger amounts), F-1240, F-1250 and F-1260, said compound being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

Said at least one compound may be present in a content of greater than or equal to 1 ppm, or greater than or equal to 2 ppm, or greater than or equal to 3 ppm, or greater than or equal to 5 ppm.

For example, said at least one compound may be present in a content of from 1 to 5 ppm; or in a content of from 5 to 10 ppm; or in a content of from 10 to 25 ppm; or in a content of from 25 to 50 ppm; or in a content of from 50 to 75 ppm; or in a content of from 75 to 100 ppm; or in a content of from 100 to 150 ppm; or in a content of from 150 to 200 ppm; or in a content of from 200 to 250 ppm; or in a content of from 250 to 300 ppm; or in a content of from 300 to 350 ppm; or in a content of from 350 to 400 ppm; or in a content of from 400 to 450 ppm; or in a content of from 450 to 500 ppm.

One embodiment relates to such compositions which comprise a plurality (two, three, four or more than four) compounds chosen from the list of additional compounds above, the content of each of said compounds being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

Each compound of this plurality may then be present in a content of greater than or equal to 1 ppm, or greater than or equal to 2 ppm, or greater than or equal to 3 ppm, or greater than or equal to 5 ppm.

For example, each compound of this plurality may be present in a content of from 1 to 5 ppm; or in a content of from 5 to 10 ppm; or in a content of from 10 to 25 ppm; or in a content of from 25 to 50 ppm; or or in a content of from 50 to 75 ppm; or in a content of from 75 to 100 ppm; or in a content of from 100 to 150 ppm; or in a content of from 150 to 200 ppm; or in a content of from 200 to 250 ppm; or in a content of from 250 to 300 ppm; or in a content of from 300 to 350 ppm; or in a content of from 350 to 400 ppm; or in a content of from 400 to 450 ppm; or in a content of from 450 to 500 ppm.

One embodiment relates to such compositions in which the content of each of the compounds of the list of additional compounds above optionally present in the composition is less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

Each compound of the list of additional compounds may then be present in a content of greater than or equal to 1 ppm, or greater than or equal to 2 ppm, or greater than or equal to 3 ppm, or greater than or equal to 5 ppm.

For example, each compound of the list of additional compounds may be present in a content of from 1 to 5 ppm; or in a content of from 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

The compositions according to the invention may especially comprise one or more compounds of the series F-220, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-220 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-220 optionally present may then be present in a content of greater than or equal to 1 ppm, or greater than or equal to 2 ppm, or greater than or equal to 3 ppm, or greater than or equal to 5 ppm. Similarly, the total content of compounds of the series F-220 in the composition may be greater than or equal to 1 ppm, or greater than or equal to 2 ppm, or greater than or equal to 3 ppm, or greater than or equal to 5 ppm.

For example, each compound of the series F-220 optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-220 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-230, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-230 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-230 optionally present may then be present in a content of greater than or equal to 1 ppm, or greater than or equal to 2 ppm, or greater than or equal to 3 ppm, or greater than or equal to 5 ppm. Similarly, the total content of compounds of the series F-230 in the composition may be greater than or equal to 1 ppm, or greater than or equal to 2 ppm, or greater than or equal to 3 ppm, or greater than or equal to 5 ppm.

For example, each compound of the series F-230 optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-230 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-240, each (except for F-240fa) being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-240 (except for F-240fa) in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-240 (except for F-240fa) optionally present may then be present in a content of greater than or equal to 1 ppm, or greater than or equal to 2 ppm, or greater than or equal to 3 ppm, or greater than or equal to 5 ppm. Similarly, the total content of compounds of the series F-240 (except for F-240fa) in the composition may be greater than or equal to 1 ppm, or greater than or equal to 2 ppm, or greater than or equal to 3 ppm, or greater than or equal to 5 ppm.

For example, each compound of the series F-240 (except for F-240fa) optionally present may be present in a content of 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-240 (except for F-240fa) in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

F-240fa may be present in an amount markedly higher than those listed above.

The compositions according to the invention may especially comprise one or more compounds of the series F-250, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-250 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-250 optionally present may then be present in a content of greater than or equal to 1 ppm, or greater than or equal to 2 ppm, or greater than or equal to 3 ppm, or greater than or equal to 5 ppm. Similarly, the total content of compounds of the series F-250 in the composition may be greater than or equal to 1 ppm, or greater than or equal to 2 ppm, or greater than or equal to 3 ppm, or greater than or equal to 5 ppm.

For example, each compound of the series F-250 optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-250 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-260, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-260 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-260 optionally present may then be present in a content of greater than or equal to 1 ppm, or greater than or equal to 2 ppm, or greater than or equal to 3 ppm, or greater than or equal to 5 ppm. Similarly, the total content of compounds of the series F-260 in the composition may be greater than or equal to 1 ppm, or greater than or equal to 2 ppm, or greater than or equal to 3 ppm, or greater than or equal to 5 ppm.

For example, each compound of the series F-260 optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-260 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-270, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-270 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-270 optionally present may then be present in a content of greater than or equal to 1 ppm, or greater than or equal to 2 ppm, or greater than or equal to 3 ppm, or greater than or equal to 5 ppm. Similarly, the total content of compounds of the series F-270 in the composition may be greater than or equal to 1 ppm, or greater than or equal to 2 ppm, or greater than or equal to 3 ppm, or greater than or equal to 5 ppm.

For example, each compound of the series F-270 optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-270 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise F-1210xa in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that F-1210xa may then be present in a content of greater than or equal to 1 ppm, or greater than or equal to 2 ppm, or greater than or equal to 3 ppm, or greater than or equal to 5 ppm.

For example, F-1210xa may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

The compositions according to the invention may especially comprise one or more compounds of the series F-1220, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1220 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-1220 optionally present may then be present in a content of greater than or equal to 1 ppm, or greater than or equal to 2 ppm, or greater than or equal to 3 ppm, or greater than or equal to 5 ppm. Similarly, the total content of compounds of the series F-1220 in the composition may be greater than or equal to 1 ppm, or greater than or equal to 2 ppm, or greater than or equal to 3 ppm, or greater than or equal to 5 ppm.

For example, each compound of the series F-1220 optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1220 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-1230 (with the exception of F-1230za and F-1230zd, which may optionally be present in larger amounts), each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1230 (except for F-1230za and F-1230zd) in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-1230 (except for F-1230za and F-1230zd) optionally present may then be present in a content of greater than or equal to 1 ppm, or greater than or equal to 2 ppm, or greater than or equal to 3 ppm, or greater than or equal to 5 ppm. Similarly, the total content of compounds of the series F-1230 (except for F-1230za and F-1230zd) in the composition may be greater than or equal to 1 ppm, or greater than or equal to 2 ppm, or greater than or equal to 3 ppm, or greater than or equal to 5 ppm.

For example, each compound of the series F-1230 (except for F-1230za and F-1230zd) optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1230 (except for F-1230za and F-1230zd) in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

F-1230za and F-1230zd may be present in amounts markedly higher than those listed above. These compounds are precursors of F-1234ze.

The compositions according to the invention may especially comprise one or more compounds of the series F-1240, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1240 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-1240 optionally present may then be present in a content of greater than or equal to 1 ppm, or greater than or equal to 2 ppm, or greater than or equal to 3 ppm, or greater than or equal to 5 ppm. Similarly, the total content of compounds of the series F-1240 in the composition may be greater than or equal to 1 ppm, or greater than or equal to 2 ppm, or greater than or equal to 3 ppm, or greater than or equal to 5 ppm.

For example, each compound of the series F-1240 optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1240 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-1250, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1250 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound of the series F-1250 optionally present may then be present in a content of greater than or equal to 1 ppm, or greater than or equal to 2 ppm, or greater than or equal to 3 ppm, or greater than or equal to 5 ppm. Similarly, the total content of compounds of the series F-1250 in the composition may be greater than or equal to 1 ppm, or greater than or equal to 2 ppm, or greater than or equal to 3 ppm, or greater than or equal to 5 ppm.

For example, each compound of the series F-1250 optionally present may be present in a content of from 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1250 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

The compositions according to the invention may especially comprise one or more compounds of the series F-1260, each being present in the composition in a content of less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm; and the total content of compounds of the series F-1260 in the composition, preferably, being less than or equal to 500 ppm; or less than or equal to 450 ppm; or less than or equal to 400 ppm; or less than or equal to 350 ppm; or less than or equal to 300 ppm; or less than or equal to 250 ppm; or less than or equal to 200 ppm; or less than or equal to 150 ppm; or less than or equal to 100 ppm; or less than or equal to 75 ppm; or less than or equal to 50 ppm; or less than or equal to 25 ppm; or less than or equal to 10 ppm; or less than or equal to 5 ppm.

It should be noted that each compound in the series F-1260 optionally present may then be present in a content of greater than or equal to 1 ppm, or greater than or equal to 2 ppm, or greater than or equal to 3 ppm, or greater than or equal to 5 ppm. Similarly, the total content of compounds of the series F-1260 in the composition may be greater than or equal to 1 ppm, or greater than or equal to 2 ppm, or greater than or equal to 3 ppm, or greater than or equal to 5 ppm.

For example, each compound of the series F-1260 optionally present may be present in a content of 1 to 5 ppm; or in a content of 5 to 10 ppm; or in a content of 10 to 25 ppm; or in a content of 25 to 50 ppm; or in a content of 50 to 75 ppm; or in a content of 75 to 100 ppm; or in a content of 100 to 150 ppm; or in a content of 150 to 200 ppm; or in a content of 200 to 250 ppm; or in a content of 250 to 300 ppm; or in a content of 300 to 350 ppm; or in a content of 350 to 400 ppm; or in a content of 400 to 450 ppm; or in a content of 450 to 500 ppm.

For example, the total content of compounds of the series F-1260 in the composition may be from 1 to 5 ppm; or from 5 to 10 ppm; or from 10 to 25 ppm; or from 25 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 450 ppm; or from 450 to 500 ppm.

Impurities that are particularly undesirable as a mixture with F-1233zdE are:
- the molecules of the series F-1215 and particularly F-1215xc and F-1215yc;
- the molecules of the series F-1224 and particularly F-1224yc, F-1224zc and F-1224ye;
- the molecules of the series F-1233 other than F-1233zdE, and particularly F-1233xf, F-1233xc and F-1233yc;
- the molecules of the series F-1242 and particularly F-1242zf.

The molecules F-1215xc, F-1215yb and F-1215yc have similar boiling points to F-1233zdE and are thus difficult to separate from it.

Due to their reactivity, the molecules that bear a group =CF2 also have risks of toxicological effects. This concerns F-1215xc and F-1215yc among the molecules mentioned above.

Consequently, it is desirable to adjust the compositions according to the invention so as to limit the presence of precursors of compounds of the series F-1215 (and especially precursors of F-1215xc and F-1215yc) therein.

Possible precursors of F-1215xc and F-1215yc by fluorination reaction are F-1210xa, F-220da (via F-1210xa) and F-220aa (via F-1210xa). Thus, advantageous compositions according to the invention:
- comprise at least one compound from among those of the series F-1210 and F-220, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
- comprise one or more compounds from among those of the series F-1210 and F-220, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
- comprise at least one compound from among F-1210xa, F-220da and F-220aa, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
- comprise one or more compounds from among F-1210xa, F-220da and F-220aa, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

Other possible precursors of F-1215xc and F-1215yc by chlorofluorination reaction (given that F-1233zdE may be manufactured by fluorination in the presence of chlorine in the gas phase) are the compounds of the series F-1220, F-1230, F-1240, F-1250 and F-1260.

Thus, advantageous compositions according to the invention:
- comprise at least one compound from among those of the series F-1220, F-1230 (except for F-1230za and F-1230zd), F-1240, F-1250 and F-1260, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
- comprise one or more compounds from among those of the series F-1220, F-1230 (except for F-1230za and F-1230zd), F-1240, F-1250 and F-1260, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

Yet other advantageous compositions according to the invention:
- comprise at least one compound from among those of the series F-1210, F-1220, F-1230 (except for F-1230za and F-1230zd), F-1240, F-1250, F-1260 and F-220, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
- comprise one or more compounds from among those of the series F-1210, F-1220, F-1230 (except for F-1230za and F-1230zd), F-1240, F-1250, F-1260 and F-220, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

F-1230za and F-1230zd may be present in amounts markedly higher than those listed above.

The molecules F-1224xe, F-1224yd, F-1224ye, F-1224zb and F-1224zc also have similar boiling points to F-1233zdE and are thus difficult to separate from it. Due to their reactivity, the molecules that bear a =CF2 group also have risks of toxicological effects. This concerns F-1224yc and F-1224zc among the molecules mentioned above. In addition, the compound F-1224ye may result, by successive fluorination, in the compound F-1225ye, which is also known for its toxicity.

Consequently, it is desirable to adjust the compositions according to the invention so as to limit the presence of precursors of compounds of the series F-1224 (and especially of precursors of F-1224yc, F-1224zc and F-1224ye) in them Possible precursors of F-1224yc by fluorination reaction are F-1220xa, F-230aa (via F-1220xa) and F-230da (via F-1220xa).

Possible precursors of F-1224zc by fluorination reaction are F-1220za, F-230fa (via F-1220za) and F-230da (via F-1220za).

Possible precursors of F-1224ye by fluorination reaction are F-1220xd, F-230da (via F-1220xd) and F-230ab (via F-1220xd).

Thus, advantageous compositions according to the invention:
- comprise at least one compound from among those of the series F-1220 and F-230, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
- comprise one or more compounds from among those of the series F-1220 and F-230, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
- comprise at least one compound from among F-1220xa, F-1220za, F-1220xd, F-230aa, F-230fa, F-230ab and F-230da, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
- comprise one or more compounds from among F-1220xa, F-1220za, F-1220xd, F-230aa, F-230fa, F-230ab and F-230da, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

Other possible precursors of F-1224yc, F-1224zc and F-1224ye by chlorofluorination reaction (given that F-1233zdE may be manufactured by fluorination in the presence of chlorine in the gas phase) are the compounds of the series F-1230, F-1240, F-1250 and F-1260.

Thus, advantageous compositions according to the invention:
   comprise at least one compound from among those of the series F-1230 (except for F-1230za and F-1230zd), F-1240, F-1250 and F-1260, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
   comprise one or more compounds from among those of the series F-1230 (except for F-1230za and F-1230zd), F-1240, F-1250 and F-1260, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

Yet other advantageous compositions according to the invention:
   comprise at least one compound from among those of the series F-1220, F-1230 (except for F-1230za and F-1230zd), F-1240, F-1250, F-1260 and F-230, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
   comprise one or more compounds from among those of the series F-1220, F-1230 (except for F-1230za and F-1230zd), F-1240, F-1250, F-1260 and F-230, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

F-1230za and F-1230zd may be present in amounts markedly higher than those listed above.

The molecules of the series F-1233 also have boiling points close to that of F-1233zdE and are thus difficult to separate from it.

Now, F-1233xf has a high tendency to polymerize and may generate a long-chain polymer which may subsequently be deposited in the form of white crystals. It is thus preferable to avoid the presence of this unstable impurity in the final compound in order to facilitate the use of F-1233zdE in the desired application.

Furthermore, the molecules F-1233xc and F-1233yc bear a =CF2 group and may have a risk of toxicological effect.

Possible precursors of F-1233xf by fluorination reaction are F-1230xf, F-1230xa, F-240db (via F-1230xf and/or F-1230xa), F-240ab (via F-1230xf) and F-240aa (via F-1230xa).

Possible precursors of F-1233xc and F-1233yc by fluorination reaction are F-1230xa, F-240db (via F-1230xa) and F-240aa (via F-1230xa).

Thus, advantageous compositions according to the invention:
   comprise at least one compound from among those of the series F-1230 (except for F-1230za and F-1230zd) and F-240 (exception made for F-240fa), in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
   comprise one or more compounds from among those of the series F-1230 (except for F-1230za and F-1230zd) and F-240 (exception made for F-240fa), the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
   comprise at least one compound from among F-1230xf, F-1230xa, F-240db, F-240ab and F-240aa, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
   comprise one or more compounds from among F-1230xa, F-240db, F-240ab and F-240aa, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

F-240fa, F-1230za and F-1230zd may be present in amounts markedly higher than those listed above.

Other possible precursors of F-1233xf, F-1233yc and F-1233xc by chlorofluorination reaction (given that F-1233zdE may be manufactured by fluorination in the presence of chlorine in the gas phase) are the compounds of the series F-1240, F-1250 and F-1260.

Thus, yet other advantageous compositions according to the invention:
   comprise at least one compound from among those of the series F-1240, F-1250 and F-1260, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
   comprise one or more compounds from among those of the series F-1230 (except for F-1230za and F-1230zd), F-1240, F-1250, F-1260 and F-240 (exception made for F-240fa), the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

F-240fa, F-1230za and F-1230zd may be present in amounts markedly higher than those listed above.

The molecule F-1242zf also has a boiling point close to that of F-1233zdE and is thus difficult to separate from it. In point of fact, this compound is liable to form F-1243zf as successive fluorination, which molecule is undesirable due to its toxicity.

Possible precursors of F-1242zf by fluorination reaction are F-1240za, F-1240zf, F-250fb (via one of the two preceding compounds), F-250da (via F-1240za) and F-250db (via F-1240zf).

Thus, advantageous compositions according to the invention:
comprise at least one compound from among those of the series F-1240 and F-250, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
comprise one or more compounds from among those of the series F-1240 and F-250, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
comprise at least one compound from among F-1240za, F-1240zf, F-250fb, F-250da and F-250db, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
comprise one or more compounds from among F-1240za, F-1240zf, F-250fb, F-250da and F-250db, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

Other possible precursors of F-1242zf by chlorofluorination reaction (given that F-1233zdE may be manufactured by fluorination in the presence of chlorine in the gas phase) are the compounds of the series F-1250 and F-1260.

Thus, yet other advantageous compositions according to the invention:
comprise at least one compound from among those of the series F-1250 and F-1260, in a content: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm; or else
comprise one or more compounds from among those of the series F-1240, F-1250, F-1260 and F-250, the total content of all these compounds being: less than or equal to 250 ppm; or from 150 to 200 ppm; or from 100 to 150 ppm; or from 50 to 100 ppm; or from 25 to 50 ppm; or from 10 to 25 ppm; or from 5 to 10 ppm; or less than or equal to 5 ppm, and for example from 1 to 5 ppm.

Impurities that are particularly undesirable as a mixture with F-1234zeE are:
the molecules of the series F-1216 and particularly F-1216yc;
the molecules of the series F-1225 and particularly F-1225ye and F-1225zc;
the molecules of the series F-1243 and particularly F-1243zf; and
the molecules of the series F-1234 other than F-1234zeE and particularly F-1234yf.

F-1216yc is toxic and has a boiling point close to that of F-1234zeE, and is thus difficult to separate from it. Its precursors by fluorination are F-1215xc and F-1215yc. The way of preventing the presence of such compounds has already been described above.

F-1225ye and F-1225zc are toxic and have boiling points close to that of F-1234zeE, and are thus difficult to separate from it. Its precursors by fluorination are F-1224ye and F-1224zc. The way of preventing the presence of such compounds has already been described above.

F-1243zf is toxic and has a boiling point close to that of F-1234zeE, and is thus difficult to separate from it. Its precursor by fluorination is F-1242zf. The way of preventing the presence of this compound has already been described above.

F-1234yf is a substance which should not be present in excessively large amount in mixture with F-1234zeE. For example, its content should be less than or equal to 500 ppm. Now, the boiling points of the two compounds are close, which makes a conventional separation difficult. The precursor of F-1234yf by fluorination is F-1233xf. The way of preventing the presence of this compound has already been described above.

It should be noted that the presence of molecules of the series F-270 may be undesirable insofar as, when a fluorination reaction is carried out in the gas phase in the presence of chlorine (for the manufacture of F-1234zeE), these molecules might by chlorinated and fluorinated to produce some of the undesirable impurities listed above.

Preparation of the Compositions According to the Invention

The manufacture of F-240fa is known, for example, from U.S. Pat. No. 5,705,779. The document proposes a process for the production of F-240fa by:
reaction of carbon tetrachloride with ethylene to produce F-250fb;
photochlorination of F-250fb to obtain F-1240fa.

The compositions according to the invention may then be obtained by performing one or more steps of separation of F-240fa with respect to the other compounds mentioned above, and especially with respect to F-240db (which is in general the majority byproduct of the chlorination) and also the other byproducts of chlorination, such as F-230 and/or F-220 and/or F-210.

These separation steps may preferably be performed by conventional absorption/washing and distillation. As an alternative to standard distillation or in combination therewith, it is also possible to envisage a separation by extractive distillation, physicochemical separations on molecular sieves, alumina or active charcoal or a membrane separation.

A first separation is generally performed using a standard distillation (column with plates, column with packing) at atmospheric pressure or under reduced pressure. The pressure chosen is less than 760 mmHg, preferentially less than 450 mmHg and more preferentially less than 200 mmHg. Inherently, the pressure of the column determines the temperature conditions for a given degree of separation. F-240fa may be recovered by performing the distillation at a temperature below 180° C., preferentially below 160° C. and more preferentially below 130° C. A simple column or a distillation train may be used. Under chosen conditions, the purity of F-240fa after distillation reaches a minimum of 99.8%.

A second separation may be performed using adsorption on zeolite or active charcoal.

The zeolites or active charcoals that may be used in the process for purifying F-240fa advantageously have a mean pore size of from 3.4 to 11 Å, preferably from 3.4 to 10 Å. If the zeolite or the active charcoal has a mean pore size of greater than 11 Å, the amount of F-240fa adsorbed increases, whereas if the mean pore size is less than 3.4 Å, the adsorption capacity of the zeolite or of the active charcoal is reduced.

Zeolite preferably has an Si/Al ratio of two or less. If the Si/Al ratio of the zeolite is greater than two, certain impurities are liable to be not selectively adsorbed. The zeolite is preferably at least one element chosen from the group consisting of 4 A molecular sieves, a 5 A molecular sieve, a 10× molecular sieve and 13× molecular sieves. Using these zeolites, the water content in F-240fa may also be simultaneously reduced.

The zeolite and the active charcoal are preferably used individually for the purpose of regenerating the adsorbent, but they may also be used as a mixture. The proportions of zeolite and of active charcoal in the mixture are not particularly important, but it is preferable to use a larger amount of zeolite, which makes it possible to reduce the water content in F-240fa.

To treat F-240fa with zeolite and/or active charcoal in the liquid phase, a batch process or a continuous process may be used. Industrially, a process that consists in continuously passing F-240fa over a fixed bed is preferable. The liquid space time velocity (LSTV) may be chosen appropriately as a function of the content of impurities to be removed and of the amount of F-240fa to be treated. In general, the space velocity is preferably from 1 to 50 $h^{-1}$. Industrially, the purification process may alternately use two adsorption towers. The treatment temperature of F-240fa is from 0° C. to 120° C., preferably from 20° C. to 80° C. If the treatment temperature is greater than 120° C., the cost of equipment may increase on account of the heating of the apparatus, whereas if the treatment temperature is below 0° C., cooling equipment may be necessary. The pressure is from 0 to 3 MPa, preferably from 0 to 1 MPa. If the pressure is greater than 3 MPa, the economic viability may reduce on account of the requirements in terms of pressure resistance of the apparatus.

A membrane separation technique may also be performed in addition to adsorption on active charcoal or on zeolite, or as an alternative to these techniques. Membrane separation may be performed in the gas phase according to a continuous process performed at low pressure, or at reduced pressure. The chosen pressure is less than 5 bar, preferentially less than 2 bar and more preferentially below atmospheric pressure. The choice of the membrane depends on the properties of the impurities to be separated from the F-240fa (difference in solubility, in diffusivity and in permeability). Membrane separation is performed at a temperature that depends on the chosen pressure, below 250° C., preferentially below 230° C. and more preferentially below 180° C.

When F-240fa containing impurities is placed in contact with zeolite and/or active charcoal in the liquid phase and/or is purified on a membrane in the gas phase under the conditions described above, F-240db may be obtained with a purity of greater than 99.9%.

Manufacture of F-1233zdE

The compositions according to the invention may be used for manufacturing F-1233zdE having desired specifications, via one or more fluorination steps.

The fluorination may be a fluorination in the liquid phase such as described in U.S. Pat. No. 8,704,017.

Alternatively and preferably, the fluorination is a catalytic fluorination in the gas phase with HF in the presence of chlorine.

The catalyst used may be, for example, based on a metal comprising a transition metal oxide or a derivative or a halide or an oxyhalide of such a metal. Examples that may be mentioned include $FeCl_3$, chromium oxyfluoride, chromium oxides (optionally subjected to fluorination treatments), chromium fluorides, and mixtures thereof. Other possible catalysts are catalysts supported on charcoal, antimony-based catalysts, aluminum-based catalysts (for example $AlF_3$ and $Al_2O_3$, alumina oxyfluoride and alumina fluoride).

A chromium oxyfluoride, an aluminum fluoride or oxyfluoride, or a supported or unsupported catalyst containing a metal such as Cr, Ni, Fe, Zn, Ti, V, Zr, Mo, Ge, Sn, Pb, Mg, Sb may generally be used.

Reference may be made in this respect to WO 2007/079 431 (on page 7, lines 1-5 and 28-32) and to FR2748473 (on page 4), to which reference is expressly made.

The catalyst is particularly preferably based on chromium and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5 to 20% by weight of chromium and from 0.5% to 20% by weight of nickel, preferably from 2% to 10% of each.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support that has or has not been subjected to an activation.

Reference may be made to WO 2009/118 628 (especially on page 4, line 30—page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF.

For example, the catalyst is preferably subjected to activation with air or oxygen and HF at a temperature of from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, of HF and of organic compounds.

The HF/organic compounds mole ratio is preferably from 2 to 40 and the oxidizing agent/organic compounds mole ratio is preferably from 0.04 to 25. The final activation temperature is preferably from 300 to 400° C. and its duration is preferably from 6 to 100 hours.

The gas-phase fluorination reaction may be performed:
with an HF/chlorinated compound mole ratio of from 1:1 to 150:1, preferably from 3:1 to 100:1 and particularly preferably from 5:1 to 50:1;
with a $Cl_2$/chlorinated compound mole ratio of from 0.01:100 to 5:100, preferably from 0.1:100 to 4:100 and more particularly preferably from 0.5:100 to 3:100;

with a contact time of from 1 to 100 s, preferably 1 to 50 s and more particularly 2 to 40 s (volume of catalyst divided by the total entering stream, adjusted to the operating temperature and pressure);

at an absolute pressure ranging from 0.1 to 50 bar, preferably from 0.3 to 15 bar;

at a temperature (temperature of the catalytic bed) of from 100 to 500° C., preferably from 150 to 450° C. and more particularly from 200 to 300° C.

The stream of products obtained from the fluorination may undergo suitable treatments (distillation, washing, etc.) so as to recover F-1233zdE in purified form and to separate out other compounds present (HCl, unreacted HF, unreacted F-240fa, and other organic compounds). One or more streams may undergo recycling.

Catalyst regeneration steps may also be envisaged, as described, for example, in WO 2012/098 421 and WO 2012/098 422, to which reference is expressly made.

The stream of F-1233zdE obtained, preferably, contains:
less than 500 ppm, or 250 ppm, or 200 ppm, or 150 ppm, or 100 ppm, or 50 ppm, or 25 ppm, or 10 ppm, or 5 ppm, of F-1233xf; and/or
less than 500 ppm, or 250 ppm, or 200 ppm, or 150 ppm, or 100 ppm, or 50 ppm, or 25 ppm, or 10 ppm, or 5 ppm, of F-1242zf; and/or
less than 500 ppm, or 250 ppm, or 200 ppm, or 150 ppm, or 100 ppm, or 50 ppm, or 25 ppm, or 10 ppm, or 5 ppm, of F-1215yc; and/or
less than 500 ppm, or 250 ppm, or 200 ppm, or 150 ppm, or 100 ppm, or 50 ppm, or 25 ppm, or 10 ppm, or 5 ppm, of F-1215xc; and/or
less than 500 ppm, or 250 ppm, or 200 ppm, or 150 ppm, or 100 ppm, or 50 ppm, or 25 ppm, or 10 ppm, or 5 ppm, of F-1224yc; and/or
less than 500 ppm, or 250 ppm, or 200 ppm, or 150 ppm, or 100 ppm, or 50 ppm, or 25 ppm, or 10 ppm, or 5 ppm, of F-1224ye; and/or
less than 500 ppm, or 250 ppm, or 200 ppm, or 150 ppm, or 100 ppm, or 50 ppm, or 25 ppm, or 10 ppm, or 5 ppm, of F-1224zc.

Preferably, these contents are obtained on conclusion of the fluorination, without (or before any) step of purification of the product stream.

Manufacture of F-1234zeE

The compositions according to the invention may be used for manufacturing F-1234zeE having desired specifications, via one or more fluorination steps starting from F-1233zdE formed in the preceding step.

The fluorination may be a fluorination in the gas phase with HF.

The catalyst used may be, for example, based on a metal comprising a transition metal oxide or a derivative or a halide or an oxyhalide of such a metal. Examples that may be mentioned include $FeCl_3$, chromium oxyfluoride, chromium oxides (optionally subjected to fluorination treatments), chromium fluorides, and mixtures thereof. Other possible catalysts are catalysts supported on charcoal, antimony-based catalysts, aluminum-based catalysts (for example $AlF_3$ and $Al_2O_3$, alumina oxyfluoride and alumina fluoride).

A chromium oxyfluoride, an aluminum fluoride or oxyfluoride, or a supported or unsupported catalyst containing a metal such as Cr, Ni, Fe, Zn, Ti, V, Zr, Mo, Ge, Sn, Pb, Mg, Sb may generally be used.

Reference may be made in this respect to WO 2007/079 431 (on page 7, lines 1-5 and 28-32), to U.S. Pat. No. 5,895,825, to which reference is expressly made.

The catalyst is particularly preferably based on chromium and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5 to 20% by weight of chromium and from 0.5% to 20% by weight of nickel, preferably from 2% to 10% of each.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support that has or has not been subjected to an activation.

Reference may be made to WO 2009/118 628 (especially on page 4, line 30—page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF.

For example, the catalyst is preferably subjected to activation with air or oxygen and HF at a temperature of from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, of HF and of organic compounds.

The HF/organic compounds mole ratio is preferably from 2 to 40 and the oxidizing agent/organic compounds mole ratio is preferably from 0.04 to 25. The final activation temperature is preferably from 300 to 400° C. and its duration is preferably from 6 to 100 hours.

The gas-phase fluorination reaction may be performed:
with an HF/chlorinated compound mole ratio of from 1:1 to 150:1, preferably from 1.5:1 to 100:1 and more particularly preferably from 2:1 to 50:1;
with a contact time of from 1 to 100 s, preferably 1 to 50 s and more particularly 2 to 40 s (volume of catalyst divided by the total entering stream, adjusted to the operating temperature and pressure);
at an absolute pressure ranging from 0.1 to 50 bar, preferably from 0.3 to 15 bar;
at a temperature (temperature of the catalytic bed) of from 100 to 500° C., preferably from 200 to 450° C. and more particularly from 250 to 400° C.

The duration of the reaction step is typically from 10 to 2000 hours, preferably from 50 to 500 hours and more particularly from 70 to 300 hours.

The oxidizing agent, preferably oxygen, may optionally be added during the fluorination reaction. The oxygen/organic compounds mole ratio may be from 0.0005 to 2, preferably from 0.01 to 1.5. The oxygen may be introduced in pure form or in the form of air or an oxygen/nitrogen mixture. The oxygen may also be replaced with chlorine.

The stream of products obtained from the fluorination may undergo suitable treatments (distillation, washing, etc.) so as to recover F-1234zeE in purified form and to separate out other compounds present (HCl, unreacted HF, unreacted F-240fa, and other organic compounds). One or more streams may undergo recycling.

Catalyst regeneration steps may also be envisaged, as described, for example, in WO 2012/098 421 and WO 2012/098 422, to which reference is expressly made.

The stream of F-1234zeE obtained, preferably, contains:
- less than 500 ppm, or 250 ppm, or 200 ppm, or 150 ppm, or 100 ppm, or 50 ppm, or 25 ppm, or 10 ppm, or 5 ppm, of F-12432f; and/or
- less than 500 ppm, or 250 ppm, or 200 ppm, or 150 ppm, or 100 ppm, or 50 ppm, or 25 ppm, or 10 ppm, or 5 ppm, of F-1225zc; and/or
- less than 500 ppm, or 250 ppm, or 200 ppm, or 150 ppm, or 100 ppm, or 50 ppm, or 25 ppm, or 10 ppm, or 5 ppm, of F-1216yc; and/or
- less than 500 ppm, or 250 ppm, or 200 ppm, or 150 ppm, or 100 ppm, or 50 ppm, or 25 ppm, or 10 ppm, or 5 ppm, of F-12434c; and/or
- less than 500 ppm, or 250 ppm, or 200 ppm, or 150 ppm, or 100 ppm, or 50 ppm, or 25 ppm, or 10 ppm, or 5 ppm, of F-1252zc; and/or
- less than 500 ppm, or 250 ppm, or 200 ppm, or 150 ppm, or 100 ppm, or 50 ppm, or 25 ppm, or 10 ppm, or 5 ppm, of F-1225ye; and/or
- less than 500 ppm, or 250 ppm, or 200 ppm, or 150 ppm, or 100 ppm, or 50 ppm, or 25 ppm, or 10 ppm, or 5 ppm, of F-1234yf.

Preferably, these contents are obtained on conclusion of the fluorination, without (or before any) step of purification of the product stream.

EXAMPLES

The following examples illustrate the invention without limiting it.

Example 1

Analysis of Two Compositions Based on F-240fa

Two compositions A and B based on F-240fa, of different purities, are considered. The first composition A results from a synthesis and from a purification in the laboratories of the applicant company. The second composition B originates from a commercial supplier, Synquest Laboratories.

The compositions in mol % of these two samples are given in table 1 below (after gas chromatography analysis).

TABLE 1

Analysis of compositions A and B

|  | Composition A | Composition B |
| --- | --- | --- |
| F-1230za | 0.055 | 0.018 |
| F-250 | 0.035 | 0.449 |
| F-240fa | 99.58 | 96.79 |
| $C_2Cl_6$ | 0.051 | 0.239 |
| F-240db | 0.157 | 2.46 |
| Others | 0.122 | 0.044 |

Example 2

Preparation of the Fluorination Catalyst 343 g of a Grace HSA alumina support, pretreated in the fixed bed at 280° C. under a HF/air mixture containing between 5 and 10% of HF, are placed in a rotary evaporator. The starting alumina is provided in the form of beads with a diameter of between 0.5 and 2 mm. Its specific surface is approximately 220 m²/g and its pore volume is 1.3 cm³/g. Furthermore, two aqueous solutions are prepared:
- one contains 81 g of methanol and 8 g of water;
- the other contains 62 g of water, 55 g of chromic acid $CrO_3$ and 130 g of nickel chloride $NiCl_2$ (dissolution of the mixture at 50° C. for 2h30).

The two solutions are introduced simultaneously and gradually onto the alumina support maintained at 40° C. and stirred. After a step of maturing under nitrogen, the catalyst is dried under nitrogen, then under vacuum at 65° C., and then at approximately 90° C. for six hours.

500 g of impregnated solid are charged to a tubular Inconel reactor. The catalyst is first of all dried while flushing with nitrogen at 320° C., at atmospheric pressure. It is subsequently fluorinated in the presence of a $HF/N_2$ (5 to 10% of HF in nitrogen) mixture at 320° C. and then up to 390° C. The HF feed is subsequently cut off. The catalyst is cooled under nitrogen.

Example 3

Gas-Phase Fluorination

The example was carried out using a continuous gas-phase fluorination pilot plant. This pilot plant comprises a reactor consisting of an Inconel tube with an internal diameter of 38 mm and with a length of 500 mm, placed vertically in a tubular electric furnace. A thermometer well with an external diameter of 6 mm is placed coaxially in the furnace and makes possible a reading of temperature along the catalytic bed using four stage thermocouples.

A coil wound around the reactor and traversed vertically from the bottom upward makes it possible to preheat the reactants before entry into the reactor. A 30 mL layer of corundum above the catalytic bed makes it possible to provide a homogeneous distribution of the gaseous reactants. A regulating valve makes it possible to maintain the desired pressure. The gas stream at the inlet and the outlet of the reactor is analyzed by gas chromatography.

An appropriate amount of solids described above is introduced into the reactor and then dried overnight in the presence of nitrogen at 250° C. and atmospheric pressure. The dried solid is subsequently activated (still at atmospheric pressure) under a stream comprising nitrogen and anhydrous hydrofluoric acid for 15 minutes before being placed under pure HF at 250° C. The pressure is subsequently very gradually regulated until 10 bar absolute are reached. The reactants (the chlorine and the composition A) are subsequently introduced. The flow rates fed are such that the HF/F-240fa mole ratio is equal to 20, the $Cl_2$/F-240fa mole ratio is equal to 0.018 and the contact time is 15 seconds. The temperature is maintained at 250° C. The composition of the gas stream exiting from the reactor is analyzed by gas chromatography and is given in table 1.

The experiment is also repeated under the same operating conditions with the sample B of F-240fa containing 2.46% of F-240db. The composition of the gas stream exiting from the reactor is analyzed by gas chromatography and is given in table 2 below in mol %.

TABLE 2

Gas-phase fluorination of compositions based on F-240fa the production of F-1233zdE

|  | Reaction with the composition A | Reaction with the composition B |
|---|---|---|
| F-1233zdE | 80.2 | 78.6 |
| F-1233zdZ | 12.8 | 11.7 |
| F-243fa | 0.7 | 0.5 |
| F-244fa | 2.6 | 3.1 |
| F-245fa | 1.4 | 2 |
| F-1233xf | 0.14 | 2.12 |
| F-1234zeE | 1.9 | 1.81 |
| F-1234zeZ | 0.1 | 0.09 |
| F-1232zd | 0.09 | 0.03 |
| F-1232za | 0.07 | 0.05 |

Example 4

Demonstration of the Polymerization of F-1233xf

A 100 mL autoclave equipped with a temperature measurement and with a pressure measurement is available. This autoclave is immersed in an oil bath, the temperature of which is regulated. 49.2 g of compound F-1233xf with a purity of 99.67% are introduced into the autoclave and the temperature of the reactor is increased to 56° C. The autogenous relative pressure is then 2.8 bar. The compound is left at temperature for 18 hours. On conclusion of this period, the reactor is brought back to ambient temperature and then depressurized toward a stainless steel trap cooled in liquid nitrogen. The cold trap is subsequently reduced in pressure and then analyzed: 99.67% of F-1233xf are obtained. The composition of the product recovered after degassing is identical to the composition of the starting material. The visual appearance of the reactor bottom, where an oily film has been deposited, is noted. The autoclave is subsequently rinsed using a dichloromethane solution, which is analyzed by liquid chromatography. The analysis reveals the presence of 1100 ppm of a compound identified by the mass spectrometry-chromatography technique: $C_9F_9H_6Cl_3$, that is to say the trimer of the compound F-1233xf.

Example 5

Demonstration of the Polymerization of F-1233xf in an Acid Medium

Example 4 is repeated with 12.1 g of F-1233xf brought into the presence of 41.6 g of HF. The mixture is left under a temperature 79° C. and a relative autogenous pressure of 7.6 bar for 18 hours. The compound collected in the cold trap after depressurization, washing in a bubbler and drying still exhibits a purity of 99.67%. Under these operating conditions, the bottom of the reactor is covered with white crystals. Approximately 1 g of these crystals could be recovered. Analyses by infrared and by NMR made it possible to identify an oligopolymeric compound consisting of $(-CClCF_3-CH_2-)_n$ groups.

The invention claimed is:

1. A composition comprising at least 99% by weight of 1,1,1,3,3-pentachloropropane and at least one additional compound selected from the group consisting of dichloropropanes, trichloropropanes, tetrachloropropanes, hexachloropropanes, heptachloropropanes, chloropropenes, dichloropropenes, trichloropropenes, tetrachloropropenes, pentachloropropenes and hexachloropropene, said at least one additional compound being present in the composition in a weight content of less than or equal to 500 ppm.

2. The composition as claimed in claim 1, in which said at least one additional compound is present in the composition in a weight content of less than or equal to 250 ppm.

3. The composition as claimed in claim 1, comprising a plurality of additional compounds selected from the group consisting of dichloropropanes, trichloropropanes, tetrachloropropanes, hexachloropropanes, heptachloropropanes, chloropropenes, dichloropropenes, trichloropropenes, tetrachloropropenes, pentachloropropenes and hexachloropropene, each of the additional compounds of said plurality of additional compounds being present in the composition in a weight content of less than or equal to 500 ppm.

4. The composition as claimed in claim 1, comprising a plurality of additional compounds selected from the group consisting of dichloropropanes, trichloropropanes, tetrachloropropanes, hexachloropropanes, heptachloropropanes, chloropropenes, dichloropropenes, trichloropropenes, tetrachloropropenes, pentachloropropenes and hexachloropropene, the total weight content of all of the additional compounds being less than or equal to 1000 ppm.

5. The composition as claimed in claim 1, comprising at least 99.5% by weight of 1,1,1,3,3-pentachloropropane.

6. The composition as claimed in claim 1, comprising at least one additional compound selected from the group consisting of hexachloropropene and heptachloropropanes, wherein the weight content of each of said additional compounds in the composition is less than or equal to 500 ppm.

7. The composition as claimed in claim 1, comprising at least one additional compound selected from the group consisting of pentachloropropenes and hexachloropropanes, wherein the weight content of each of said additional compounds in the composition is less than or equal to 500 ppm.

8. The composition as claimed in claim 1, comprising at least one additional compound selected from the group consisting of tetrachloropropenes wherein the weight content of each of said additional compounds in the composition is less than or equal to 500 ppm.

9. The composition as claimed in claim 1, comprising at least one additional compound selected from the group consisting of 2,3,3,3-tetrachloropropene and 1,1,2,3-tetrachloropropene, wherein the weight content of each of said additional compounds in the composition is less than or equal to 500 ppm.

10. The composition as claimed in claim 1, comprising at least one additional compound selected from the group consisting of trichloropropenes and tetrachloropropanes, wherein the weight content of each of said additional compounds in the composition is less than or equal to 500 ppm.

11. The composition as claimed in claim 1, comprising at least one additional compound selected from the group consisting of 1,1,3-trichloropropene, 3,3,3-trichloropropene, 1,1,1,3-tetrachloropropane, 1,1,2,3-tetrachloropropane and 1,1,1,2-terachloropropane, wherein the weight content of each of said compounds in the composition is less than or equal to 500 ppm.

\* \* \* \* \*